United States Patent [19]

Sakurai et al.

[11] Patent Number: 4,540,479

[45] Date of Patent: Sep. 10, 1985

[54] OXYGEN SENSOR ELEMENT WITH A CERAMIC HEATER AND A METHOD FOR MANUFACTURING IT

[75] Inventors: Shigenori Sakurai; Takashi Kamo; Toshinobu Furutani, all of Toyota, Japan

[73] Assignee: Toyota Jidosha Kabushiki Kaisha, Toyota, Japan

[21] Appl. No.: 431,366

[22] Filed: Sep. 30, 1982

[30] Foreign Application Priority Data

Mar. 26, 1982 [JP]  Japan ................................. 57-48367

[51] Int. Cl.³ ............................................ G01N 27/46
[52] U.S. Cl. .................................. 204/427; 228/124; 219/543; 219/544; 219/553
[58] Field of Search ............... 204/195 S, 421–429; 338/300, 308; 219/543, 544, 553; 228/122, 124

[56] References Cited

U.S. PATENT DOCUMENTS

| | | | |
|---|---|---|---|
| T979,002 | 2/1979 | Akiyama et al. | 204/195 S |
| 3,006,069 | 10/1961 | Rhoads et al. | 228/124 |
| 3,089,234 | 5/1963 | Deevy | 228/124 |
| 3,302,961 | 2/1967 | Franklin | 228/124 |
| 3,928,161 | 12/1975 | McIntyre et al. | 204/195 S |
| 4,035,613 | 7/1977 | Sagawa et al. | 219/552 |
| 4,037,773 | 7/1977 | Record | 228/122 |
| 4,178,222 | 12/1979 | Murphy et al. | 204/195 S |
| 4,199,423 | 4/1980 | Mann | 204/429 |
| 4,212,720 | 7/1980 | Maurer et al. | 204/195 S |
| 4,219,399 | 8/1980 | Gruner et al. | 204/195 S |
| 4,328,296 | 5/1982 | Tanaka et al. | 204/195 S |
| 4,402,820 | 9/1983 | Sano et al. | 204/425 |

Primary Examiner—T. Tung
Attorney, Agent, or Firm—Oblon, Fisher, Spivak, McClelland & Maier

[57] ABSTRACT

An oxygen sensor element with a ceramic heater, having a cylindrical element body formed of an oxygen ion permeable solid electrolyte with one end closed, inner and outer electrodes formed on the inner and outer surfaces of the element body, and an electrode protective layer covering at least one of the inner and outer electrodes, the ceramic heater including a bar-like ceramic core member, a ceramic covering layer which covers the outer surface of the ceramic core member and a heating member disposed in the interface between the core member and the covering layer.

11 Claims, 7 Drawing Figures

OXYGEN SENSOR ELEMENT WITH A CERAMIC HEATER AND A METHOD FOR MANUFACTURING IT

BACKGROUND OF THE INVENTION (1) Field of the invention:

The present invention relates to an oxygen sensor element with a ceramic heater and a method for manufacturing it.

(2) Prior art:

There have been conventionally known oxygen sensors employing an oxygen ion permeable solid electrolyte as a detector of the oxygen concentration in the exhaust gas from the internal combustion engine. In such a type of oxygen sensor, for instance, a cylindrical oxygen sensor element body with one end closed is made of zirconia or the like; electrodes are formed on the inner and outer surfaces of the element; and an electrode-protecting layer is formed at least on the outer electrode while a gas to be measured is allowed to be in contact with the outer electrode, a reference gas is introduced into the interior of the element so as to be in contact with the inner electrode of the element. Thus, the electromotive force is induced due to the difference in oxygen concentration between the reference gas and the gas to be measured, thereby enabling the oxygen concentration of the gas to be measured though the measurement of the electromotive force. A signal representative of the oxygen concentration of the gas measured by the oxygen sensor is transmitted to the fuel supply system, so that feedback control of the air-fuel ratio in the vicinity of the theoretical value is provided.

However, there is a social demand for low fuel consumption in the automobiles. For this purpose, countermeasures for reducing the wearing-out and weight of the automobiles have been taken. However, such countermeasures inevitably lower the exhaust gas temperature. In cases where the exhaust gas temperature is lower, the performance of the oxygen sensor is deteriorated because the oxygen sensor element is not fully heated. Further, it is difficult to control the air-fuel ratio near the theoretical value. Thus, the purification of the exhaust gas is not carried out effectively.

For the purpose of solving the above problems, there have been conventionally proposed oxygen sensors with the heater element (Japanese Patent Application Laid Open Nos. 44999/1980, 134497/1979 and 47753/1981). Such oxygen sensors are broadly classified into two types: one in which the coil-like metal heater is inserted into the inside of the sensor element; and the other in which a bar-like ceramic heater is inserted into the inside of the sensor element.

In the case of the oxygen sensor in which the metal heater is inserted into the inside of the oxygen sensor element, the metal heater of a metal other than Pt is oxidized and therefore, has low life of span. Further, the concentration of the partial pressure of the oxygen in the inside of the sensor element fluctuates due to the oxidation reaction of the metal, and an accurate signal can not be obtained.

There has been also proposed an oxygen sensor in which the metal heater is disposed inside of the thin metal cylindrical body and MgO or the like is filled into the space between the cylindrical body and the heater. Such a heater can prevent the heater itself from being oxidized and consequently the life span of the heater is prolonged. On the other hand, however, the fluctuation of the partial pressure of the oxygen inside of the element can not be avoided due to the oxidation of the metal cylindrical body.

Moreover, in an case of the oxygen sensor employing the ceramic heater in which the heating member is provided on the both sides of the plate-like base of ceramic, since the plate-like ceramic heater base is inserted into the inside of the sensor element, the thickness and width of the base is restricted. Thereby, a satisfactory heating capacity can not necessarily be obtained. If the heater base is designed larger to produce an adequate amount of heat, it is necessary to make larger the inner diameter of the inside of the sensor element to secure the housing space for such a larger heater. In this case the sensor element become more bulky, the oxygen sensor is accordingly larger, with the result of the high cost and enlargement of the space for mounting the oxygen sensor. Besides, the distance between the surface of the plate-like ceramic heater housed inside of the sensor element and the inner surface of the element becomes larger. As a result, the sensor element can not be effectively heated.

SUMMARY OF THE INVENTION

An object of the present invention is to provide an oxygen sensor element with a heater which is free from the drawbacks encountered in conventional oxygen sensor elements.

More specifically, the object of the present invention is to provide a heater which can effectively heat the oxygen sensor element thereby to enhance the performance of the sensor element at low temperatures.

Another object of the present invention is to provide an oxygen sensor element with a heater which withstands longer use in service.

Still a further object of the present invention is to provide an oxygen sensor element which is prevented from becoming bulky while the heating body is designed larger.

Still another object of the present invention is to provide a method of manufacturing such an oxygen sensor element.

According to the present invention, a heater comprising a bar-like ceramic core, a covering layer surrounding the outer circumference of the ceramic core, and the heating member disposed in the interface between them is housed inside of the sensor element.

The sensor element according to the present invention is manufactured by providing a metallized layer on a part of the outer circumference of the ceramic heater as constituted above, placing a fitting member on the outer circumference of the metallizing layer of the ceramic layer, integrally joining the fitting member and the ceramic heater by means of brazing, and engaging the fitting member thus jointed with the inner circumference of the opening of the oxygen sensor element.

These and other objects and advantages of the present invention will become apparent upon the reading of the description of the preferred embodiments of the invention in conjunction with the attached drawings in which:

DETAILED DESCRIPTION OF THE PREFERRED EMBODIMENTS

Figure 1:
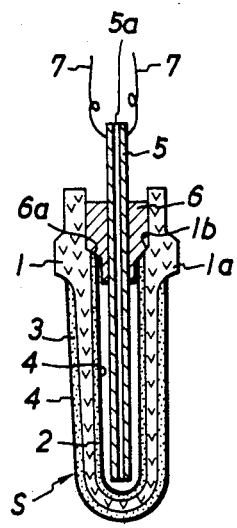
FIG. 1 is a sectional view of an oxygen sensor element with a heater according to the present invention.

The present invention will now be described in more detail by way of example based on the embodiments shown in the drawings. However, they are merely illustrative of the present invention and are not intended to limit the scope of the present invention.

FIG. 1 is a sectional view of an oxygen sensor element S according to the present invention. A reference numeral 1 is designates a tube-like sensor element body with one end closed which has a shoulder 1a provided on the outer side surface of the body 1 near the opening and projecting outwardly. The body 1 also has a taper portion 1b which is positioned on the inner side surface near the opening and becomes smaller in diameter in the direction towards the closed end. The element body is made of, for instance, zirconia stabilized with yttrium oxide ($Y_2O_3$). Reference numerals 2 and 3 designate metal electrodes provided on the inner and outer surfaces of the element body 1. The inner electrode 2 may be formed on the whole inner surface of the element body 1, or it may be formed only on a part of the inner surface. In the latter case, it is desirable to provide extension at the upper portion of the taper portion 1b so as to be connected to the metal electrode 2. The outer electrode 3 may be also formed on the whole outer surface of the element body 1, but it may be formed only on a part thereof so long as the outer electrode 3 is provided up to the upper portion of the shoulder 1a. Each metal electrode 2, 3 is a layer comprising a metal having heat-resistance and catalytic activity, such as Pt, Rh, Ag or the like. Reference numerals 4, 4' designate porous coated layers comprising inorganic material for the protection of the inner electrode 2 and outer electrode 3. The protective layer 4' on the inner surface of the element body 1 may be omitted without deteriorating the performance of the sensor elements.

A ceramic heater 5 is fitted to the opening of the sensor element S thus constituted via a metal fitting member 6 having an almost cylindrical form in such a manner that the axis of the metal fitting is in alignment with the axis of the sensor elements. The ceramic heater 5 has a longitudinally elongated cylindrical form, and it is made of alumina or the like having an insulating property. It has a hollow portion 5a running axially throughout into which a reference gas is introduced into the inside of the sensor elements. Inside of the wall of the cylindrical body of the heater 5 is embedded a heating member described hereinbelow. The fitting member 6 is made of metal, and has an inner diameter commensurate with the outer diameter of the ceramic heater 5 and an outer profile commensurate with the opening of the upper inner portion of the element body 1. The fitting member 6 is fitted to the opening of the sensor elements in such a way that it is engaged with the outer circumference of the heater 5 for securing thereof and the lower face of a taper 6a of the fitting member 6 is engaged with the upper portion of the taper portion 1b of the element body 1. By so doing, the inner electrode 2 of the sensor element S is in contact with the fitting element 6, thereby permitting the inside potential to be taken out. Reference numerals 7, 7 designate the lead wires to impress the voltage for the heating member embedded in the inside of the ceramic heater 5.

Figure 2:
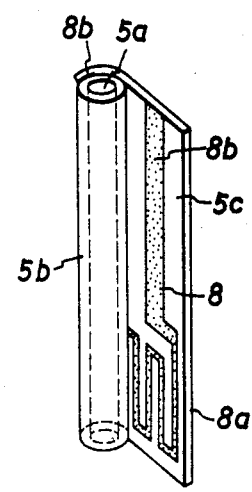
FIGS. 2 to 5 are schematic views illustrating the manufacturing process of an oxygen sensor element with a heater according to the present invention.
Figure 3:
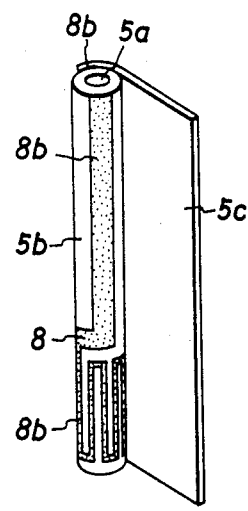

The ceramic heater 5 in a cylindrical form is, for instance, manufactured as shown in FIGS. 2 and 3.

In FIG. 2, a reference numeral 5b designates a bar-like core member having a through-hole 5a in its center. A reference numeral 5c designates a ceramic sheet in a rectangular form having enough width to cover the outer circumference of the core member 5b and enough length and almost the same longitudinal length as that the core member 5b. On the inner surface of the ceramic sheet 5c is formed a band-like metal heating member 8. The metal heating member 8 is composed of a heating portion 8a in a continuously undulatory form on the lower inner portion of the ceramic sheet 5c and a pair of conductive portions 8b and 8b which are connected to the heating portion 8a and extend up to the upper end of the ceramic sheet 5c. The metal heating member may be formed, for instance by printing in a desired profile on the ceramic sheet 5c prior to firing, a paste prepared by admixing the powder of heat-resistant metal such as Pt, Pt based alloy, W or the like into an organic solvent. Thereafter, similarly to the above, the ceramic sheet 5c is wound around the outer surface of the ceramic core 5b in such a manner that the heating member 8 is located to face the outer surface of the core member 5b. Then, the whole ceramic heater 5 is heated by firing to form a ceramic heater 5.

The heating member 8 may be formed on the outer circumference of the ceramic core 5b as shown in FIG. 3. In such a case, the metallic paste is printed in a desired profile on the outer surface of the ceramic core 5b to form a heating member consisting of a heating portion 8a and a conductive portion 8b. Then, the ceramic sheet 5c is wounded around the core member 5b prior to firing. The ceramic sheet 5c and ceramic core 5b thus combined are simultaneously fired.

Figure 4:
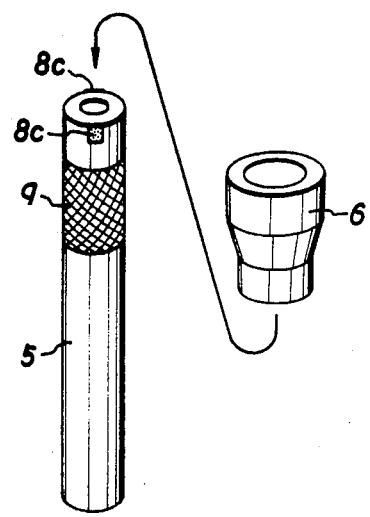

Next, as shown in FIG. 4, the ceramic heater 5 is provided at the upper outer circumference with input portions 8c, 8c for electrical connection to the conductive portions 8b, 8b. The input portions 8c and 8c are formed similarly to the method for forming the heating and conductive portions. A metallized layer 9 is formed on the upper outer surface of the ceramic heater over its circumference. The a metallized layer 9 may be formed by applying a mixed paste of, for instance, Mo-Mn or Mo-W to a desired portion of the ceramic heater 5 and then firing it under nonoxidizing atmosphere such as decomposed ammonium gas.

Figure 5:
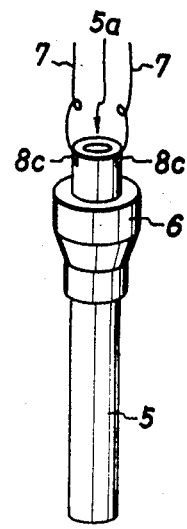

After the formation of the metallized layer 9, the fitting member 6 is fitted to the ceramic heater 5 in such a manner that the inner surface of the fitting member 6 is in contact with the metallized layer 9. After the location of the fitting member 6 on the ceramic heater 5, brazing is effected to join and secure them together. The brazing is carried out by employing a conventional brazing material, such as silver braze, Ni braze or the like. The metallized layer 9 may be formed simultaneously with the production of the ceramic heater 5. For instance, the ceramic sheet 5c as not fired is wound around the core member 5b as not fired and input portions 8c, 8c and metallized layer 9 are formed by using a paste, followed by firing and braking. FIG. 5 shows the ceramic heater 5 securing the fitting member 6 on its outer circumference.

Joining the ceramic heater 5 and the fitting member 6 as mentioned above enables the deformation during sintering to become smaller and therefore strengthen the joint between them as compared with the joining by means of inorganic adhesive agent. Further, since the adhesive agent is not likely to be damaged even after a long service at an elevated temperature no peeling-off takes place due to vibration. As mentioned above, in case the formation of the metallized layer 9 is done simultaneously with sintering of the ceramic heater 5, the manufacturing process can be simplified.

The ceramic heater 5 fitted to the fitting member 6 is placed into the sensor element S by inserting the fitting member 6 into the opening element of the body 1 as shown in FIG. 1.

Figure 6:
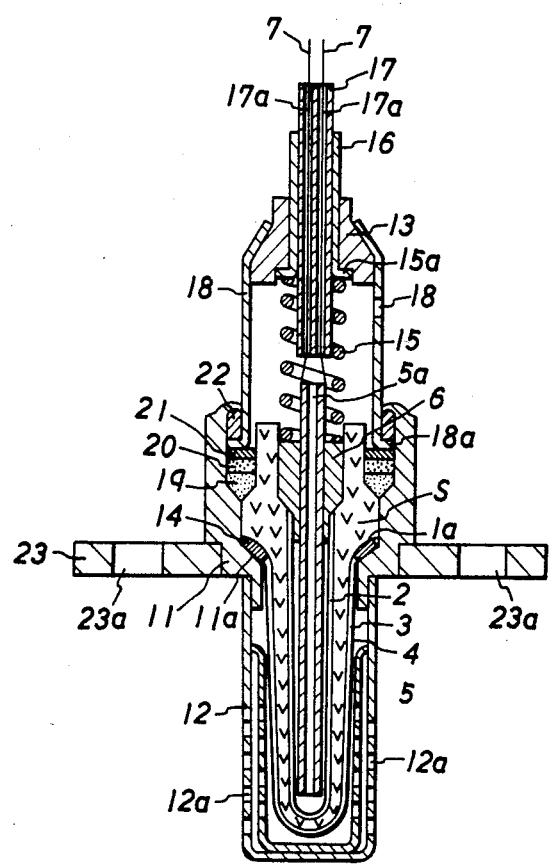
FIG. 6 is a sectional view of an oxygen sensor mounting an oxygen sensor element with a heater according to the present invention.

FIG. 6 is a sectional view of a sensor with the sensor element 5 as constructed in FIG. 1. In the Figure, a reference numeral 11 designates an almost cylindrical housing having a stepped portion 11a which the shoulder 1a of the sensor element body 1 is to engage. A protective cover 12 is provided at the lower end of the housing 11 to protect the projecting portion of the sensor element S. The protective cover 12 is made of heat-resistant steel plate and the side wall of it is provided with through-holes 12a, 12a, through which a gas to be measured is introduced inside of the protective cover 12 to contact the outer surface of the element S. A reference numeral 14 designates a cushioning member disposed between the lower face of the shoulder 1a of the element body 1 and the upper surface of the stepped portion 11a of the housing for the purpose of the cushioning and providing a sealing function therebetween. A reference numeral 15 designates a coil spring made of a heat-resistant metal the lower end of which is in contact with the upper face of the fitting member 6 while the upper end of the coil spring 15 is in contact with a lower face of a flange 15a of an outer terminal 16 formed as cylindrical hollow heat-resistance metal member located upwardly of the sensor element S. By such a construction, the potential generated on the inner electrode 2 of the element S is transmitted out through the fitting metal member 6, the coil spring 15 and the outer terminal 16.

A bushing 17 is inserted inside of the outer terminal 16. The bushing 17 is formed, for instance, from heat-resistant insulating material such as alumina or the like, and it has two through-holes 17a in the axial direction through which the lead wires 7, 7 of the ceramic heater 5 are passed. The lead wires 7, 7 (input wires) are connected to the input portion of the ceramic heater 5 to impress the ceramic heater 5 for production of the heat in the heating portion.

A reference numeral 18 designates an upper protective tube mounted on the upper portion of the housing 11 in such a manner that after a lower flange 18a of it is placed on a graphite ring 19, a talc ring 20 and a press ring 21 disposed in a space defined by the shoulder 1a and the housing 11, the upper portion of the housing 11 is caulked radially and inwardly, with a location ring 22 disposed on the flange 18a. The upper portion of the protective tube 18 is designed taper to become narrower in diameter in an ascending direction. In assembling, the bushing 17 is urged downwardly via a bushing 13 mounted on the outer circumference of the outer terminal 16 by means of the protective tube 18. By so assembling, the coil spring 15 is pressed downwardly and held between the outer terminal 16 and the fitting metal member 6 in such a state that the spring 15 may hold an appropriate spring force. The outer terminal 16 and the bushing 17 are so urged upwardly by means of the spring force of the spring 15 that they may come in press contact with the protective tube 18 through bushing 13. At the same time, the fitting metal member 6 is brought into press contact with the opening of the element body 1 by means of the spring force of the spring 15. Thereby, the assembling of the parts is assured and the electrical contact is also improved. In FIG. 6, a reference numeral 18b designates a through-hole provided in the upper side wall of the protective tube 18 through which an outer atmosphere or reference gas is introduced. The introduced atmosphere comes into the interior of the sensor element S through the hollow portion 5a of the ceramic heater 5 so that the partial pressure in the interior of the element S is kept constant. As mentioned above, the potential generated in the inner electrode 2 of the sensor element S is taken outside through the fitting metal member 6, the coil spring 15 and the outer terminal 16. On the other hand, the potential generated in the outer electrode 3 is taken outside through the graphite ring 19, and the housing 11. The talc ring 20 serves to interrupt the contact between the graphite ring 19 and the outer atmosphere, thereby preventing the wearing-out of the graphite ring 19. The input wires 7, 7 for the ceramic heater 5 pass through the through-holes 17a, 17a of the bushing 17 disposed in the outer terminal 16, so that they are not in contact with each other and are not in contact with the signal transmitting circuit for the inner electrode 2. The oxygen sensor thus constructed is attached to an exhaust pipe (not shown) by screwing a flange 23 attached to the outer circumference of the housing 11 in such a manner that the projection of the sensor element S may face with the interior of the exhaust pipe. Reference numerals 23a, 23a are holes for screwing.

When the oxygen sensor thus constructed is put in service, the oxygen sensor which is attached at a predetermined portion of the exhaust pipe is heated by impressing an electric current through the input wires 7, 7. Thus, the sensor element S is heated at an appropriate temperature, for instance, from about 500 to about 700° C. The reference gas to be filled into the interior of the sensor element S is introduced from the outside through the through-hole 18b of the protective tube 18 and the hollow portion 5a of the ceramic heater 5, while the gas to be measured is brought into contact with the outer surface of the sensor element S through the through-holes 12a, 12a, of the protective cover 12. The difference in potential between the inner and outer electrodes 2, 3 of the sensor element S is produced due to the difference in the oxygen partial pressure between the reference gas and the gas to be measured which is in contact with the sensor element S, and the potential is taken out through the inner electrode signal circuit and the outer electrode circuit, so that the electromotive force between the inner and outer electrodes 2, 3 is measured by means of an appropriate circuit (not shown).

The oxygen sensor element with a heater 5 according to the present invention is not limited to the ones specifically described above. For instance, the core material 5b of the ceramic heater 5 is a bar-like solid member. When the solid member is employed, the communication between the interior of the element and the outer atomosphere may be assured in such a manner that at a part of the inner surface of the fitting member 6 there is provided a notched groove such that the atmospheric gas may be allowed to pass through a through-hole defined by the outer surface of the ceramic heater 5 in the fitting member 6 and the notched groove when the ceramic heater 5 is secured to the fitting metal member 6. Furthermore, an insulating fitting member may be employed instead of the fitting metal member 6. In such a case, it is necessary to provide a metal tube for taking out the potential of the inner electrode 2. Meanwhile, the ceramic heater 5 and the element body 1 may be so designed that the outer circumference of the ceramic heater 5 and the inner circumference of the element body 1 may be engageable with each other and that they may be joined with each other via a cushioning member.

Figure 7:
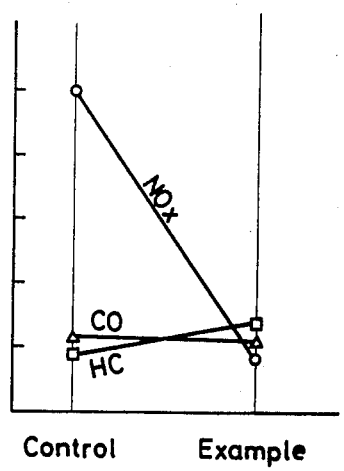
FIG. 7 is a diagram illustrating test results on the oxygen sensor elements and control.

The oxygen sensor constructed as shown in FIG. 6 and the same oxygen sensor with no ceramic heater were attached to the exhaust pipe of the 2000 cc engine having 6 cylinders. Thereafter, the emission value with respect to each component in the case of 10 mode running was measured. (The minimum temperature of the exhaust gas was 270° C.) The emission values thus measured are shown in FIG. 7. The voltage for impressing electrical current to the heater was set at 6.5 voltages×2 amperes.

As obvious from FIG. 7, the automobile to which the oxygen sensor with a heater according to the present invention is attached exhibits excellent purification rates with respect to three components of hydrocarbon (HC), carbon monoxide (CO) and nitrogen oxide ($NO_x$) even at low exhaust gas temperature. On the other hand, the automobile to which the oxygen sensor with no heater exhibits high emission value with respect to $NO_x$, and therefore satisfactory purification of the exhaust gas was not attained.

As seen from the foregoing description, according to the present invention, the performance of the oxygen sensor can be improved. Further, since the ceramic heater is designed in a bar-like shape, the area in which the heater member can be formed is increased with no need to increase the inner diameter of the sensor element. Thus, bulkiness of the sensor element is avoided. In addition, the oxygen sensor according to the present invention has the advantage that the inner surface of the sensor element can be uniformly heated because the ceramic heater is formed in a bar-like shape.

Meanwhile, the heating member is covered with a ceramic layer so that it is not exposed to the reference gas inside of the sensor element. Thereby, the oxidation of the heating member is prevented with increased durability and fluctuation of the oxygen partial pressure inside of the element is diminished. Consequently, the fidelity of the output signals from the oxygen sensor is improved.

The present invention has been described based on an oxygen concentration cell type sensor adapted to measure the change in electromotive force produced in the sensor element due to the difference in oxygen partial pressure between the reference gas inside of the element and the gas to be measured outside of the element, but it is not limited to this type. For instance, the present invention is applicable to a limit electric current type oxygen sensor adapted to measure the limit electric current produced in the sensor element due to the oxygen concentration in the gas to be measured so long as the sensor element itself is designed in a shape as shown in FIG. 1.

While the preferred embodiments have been described in foregoing, it is to be understood that variations and modifications will be made by those skilled in the art to which the present invention pertains without departing from the spirit of the invention.

What is claimed as new and desired to be secured by Letters Patent of the United States is:

1. An oxygen sensor element having a ceramic heater, said oxygen sensor element comprising:
   (a) a hollow, cylindrical sensor element body made of an oxygen permeable material, said sensor element body having one closed end and one open end;
   (b) inner and outer electrodes provided on the inner and outer surface of said sensor element body, respectively;
   (c) a fitting member made of metal, said fitting, member being mounted in the open end of said sensor element body in electrical contact with said inner electrode, said fitting member having an axial opening therethrough;
   (d) a ceramic heater mounted in the axial opening in said fitting member, said ceramic heater having a first end and a second end, the first end of said ceramic heater axially projecting from said fitting member into said hollow, cylindrical sensor element body, said ceramic heater comprising:
      (i) a bar-like ceramic core, said bar-like ceramic core having an axial opening therethrough for introducing a reference gas into the inside of said hollow, cylindrical sensor element body so as to be in contact with said inner electrode;
      (ii) a ceramic layer disposed around said ceramic core and in contact with the outer surface of said ceramic core;
      (iii) a metallized layer formed on a portion of the outer surface of said ceramic layer, said ceramic heater being joined to said fitting member by brazing said metallized layer to said fitting member, thereby longitudinally positioning said ceramic heater; and
      (iv) a heating member hermetically sealed between said ceramic core and said ceramic layer, said heating member having a heating portion positioned near the end of said ceramic heater remote from said fitting member; and
   (e) first means for exposing said outer electrode to a gas the oxygen content of which is to be sensed.

2. An oxygen sensor element as recited in claim 1 wherein said first means comprises an oxygen permeable protective layer provided on the outer surface of said outer electrode.

3. An oxygen sensor element as recited in claim 1 or claim 2 wherein:
   (a) the outer surface of said fitting member is stepped, having a greater diameter at the end thereof near the open end of said sensor element and a lesser diameter at the end thereof remote from the open end of said sensor element body, and
   (b) the open end of said sensor element body is internally stepped to match the outer surface of said fitting member,
   whereby said fitting member may be spring-biased into axially abutting engagement with said sensor element body.

4. An oxygen sensor element as recited in claim 3 wherein said ceramic core is cylindrical in shape.

5. An oxygen sensor element as recited in claim 4 wherein the second of said ceramic heater extends through said fitting member and projects from said fitting member away from said sensor element body.

6. An oxygen sensor element as recited in claim 3 wherein the second of said ceramic heater extends through said fitting member and projects from said fitting member away from said sensor element body.

7. An oxygen sensor element as recited in claim 1 or claim 2 wherein said ceramic core is cylindrical in shape.

8. An oxygen sensor element as recited in claim 5 wherein the second of said ceramic heater extends through said fitting member and projects from said fitting member away from said sensor element body.

9. An oxygen sensor element as recited in claim 1 or claim 2 wherein the second end of said ceramic heater extends through said fitting member and projects from said fitting member away from said sensor element body.

10. A process for manufacturing an oxygen sensor element having a ceramic heater, said oxygen sensor element comprising:
  (a) a hollow, cylindrical sensor element body made of an oxygen permeable material, said sensor element body having one closed end and one open end;
  (b) inner and outer electrodes provided on the inner and outer surfaces of said sensor element body, respectively;
  (c) a fitting member made of metal, said fitting member being mounted in the open end of said sensor element body in electrical contact with said inner electrode, said fitting member having an axial opening therethrough;
  (d) a ceramic heater mounted in the axial opening in said fitting member, said ceramic heater having a first end and a second end, the first end of said ceramic heater axially projecting from said fitting member into said hollow, cylindrical sensor element body, said ceramic heater comprising:
    (i) a bar-like ceramic core, said bar-like ceramic core having an axial opening therethrough for introducing a reference gas into the inside of said hollow, cylindrical sensor element body so as to be in contact with said inner electrode;
    (ii) a ceramic layer disposed around said ceramic core and in contact with the outer surface of said ceramic core; and
    (iii) a heating member hermetically sealed between said ceramic core and said ceramic layer, said heating member having a heating portion positioned near the end of said ceramic heater remote from said fitting member; and
  (e) first means for exposing said outer electrode to a gas the oxygen content of which is to be sensed,
said process comprising the steps of:
  (f) providing a metallized layer on a portion of the outer surface of said ceramic layer;
  (g) positioning said fitting member over said metallized layer;
  (h) integrally bonding said ceramic heater to said fitting member by means of brazing said metallized layer to said fitting member, thereby longitudinally positioning said ceramic heater with respect to said fitting member; and
  (i) mounting said fitting member inside the open end of said hollow, cylindrical sensor element body.

11. A process as recited in claim 10 wherein:
  (a) the outer surface of said fitting member is stepped, having a greater diameter at the end thereof near the open end of said sensor element body and a lesser diameter at the end thereof remote from the open end of said sensor element body, and
  (b) the open end of said sensor element body is internally stepped to match the outer surface of said fitting member,
said process comprising the further step of spring biasing said fitting member into axially abutting engagement with said sensor element body.

* * * * *